US012591972B2

(12) United States Patent
Imai et al.

(10) Patent No.: US 12,591,972 B2
(45) Date of Patent: Mar. 31, 2026

(54) DEVICE FOR INFERRING MATERIAL DENSITY IMAGE, CT SYSTEM, STORAGE MEDIUM, AND METHOD OF CREATING TRAINED NEURAL NETWORK

(71) Applicant: GE Precision Healthcare LLC, Waukesha, WI (US)

(72) Inventors: Yasuhiro Imai, Hino (JP); Yuri Teraoka, Hino (JP); Ayako Matsumi, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 406 days.

(21) Appl. No.: 18/458,030

(22) Filed: Aug. 29, 2023

(65) Prior Publication Data
US 2024/0070861 A1 Feb. 29, 2024

(30) Foreign Application Priority Data
Aug. 31, 2022 (JP) ................................. 2022-138638

(51) Int. Cl.
*G06T 7/00* (2017.01)
*A61B 6/03* (2006.01)

(52) U.S. Cl.
CPC ............ *G06T 7/0012* (2013.01); *A61B 6/032* (2013.01); *G06T 2207/10072* (2013.01); *G06T 2207/10081* (2013.01); *G06T 2207/10116* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2020/0163637 A1* 5/2020 Choi ..................... A61B 6/5205
2020/0205751 A1* 7/2020 Taguchi ............... A61B 6/4452
2020/0273215 A1* 8/2020 Wang ........................ G06N 3/09
2021/0007691 A1* 1/2021 Prabhu Verleker .... A61B 6/405
2021/0110583 A1* 4/2021 Lee ........................ A61B 6/482
2021/0372951 A1* 12/2021 Ramani ............... G01N 23/046

* cited by examiner

*Primary Examiner* — Mark R Milia

(57) ABSTRACT
A device including one or more processor for performing an operation, the operation including inputting a CT image into a first trained neural network, causing the first trained neural network to infer a virtual monochromatic X-ray image based on the CT image, generating a water density image and iodine density image based on the CT image and the virtual monochromatic X-ray image inferred by the first trained neural network, inputting the water density image and iodine density image into a second trained neural network, and causing the second trained neural network to infer a water density image and iodine density image based on the water density image and iodine density image.

13 Claims, 13 Drawing Sheets

Contrast agent 112          71 72 73 7n

Fig. 12

DEVICE FOR INFERRING MATERIAL DENSITY IMAGE, CT SYSTEM, STORAGE MEDIUM, AND METHOD OF CREATING TRAINED NEURAL NETWORK

CROSS-REFERENCE TO RELATED APPLICATIONS

This application claims priority to Japanese Application No. 2022-138638, filed on Aug. 31, 2022, the disclosure of which is incorporated herein by reference in its entirety.

TECHNICAL FIELD

The present invention relates to a device for inferring a material density image, a CT system for inferring a material density image, a storage medium in which a command for inferring a material density image is stored, and a method of creating a trained neural network for inferring a material density image.

BACKGROUND

A CT system is known as a medical device that noninvasively images a subject body. CT systems are widely used in hospitals and other medical facilities because they can acquire tomographic images of a subject body in a short scanning time.

SUMMARY OF THE INVENTION

Single energy CT (SECT) is a well-known imaging technique for CT systems. Single energy CT is a method of obtaining a CT image of a subject body by applying a prescribed voltage (for example, 120 kVp) to a cathode-anode tube of an X-ray tube to generate X-rays. However, with single energy CT, the CT values may be close even for different materials, making it difficult to identify different materials.

Thus, dual energy CT (DECT) technology is being researched and developed (see Patent Document 1). Dual energy CT is a technique that uses X-rays in different energy regions to distinguish materials, and dual energy CT-compatible CT systems are commercially available.

However, dual energy CT devices are generally more expensive than single energy CT devices, and although some medical institutions have introduced CT systems compatible with single energy CT, many medical institutions have not introduced CT systems compatible with dual energy CT. Thus, even in medical institutions that do not have CT systems compatible with dual energy CT, a technology has been researched and developed to infer a virtual monochromatic X-ray image from images acquired by single energy CT and to generate a material density image based on the inferred virtual monochromatic X-ray image.

In general, however, a virtual monochromatic X-ray image inferred based on single energy CT data is somewhat less accurate in terms of CT values than a virtual monochromatic X-ray image calculated based on dual energy CT data. Therefore, when a material density image is calculated based on the virtual monochromatic X-ray image inferred from single energy CT data, the accuracy of the calculated material density image is limited.

For these reasons, there is a need for a technology that can achieve a high-quality material density image using a CT system of single energy CT.

Aspect 1 of the present invention is a device, including one or more processors for performing an operation, the operation includes inputting a CT image generated based on single energy CT data collected from a subject body into a first trained neural network, the first trained neural network being created by a first neural network performing learning using a plurality of virtual monochromatic X-ray images in a training phase, causing the first trained neural network to infer a virtual monochromatic X-ray image based on the CT image, generating a first material density image expressing the density of a first reference material and a second material density image expressing the density of a second reference material based on the CT image and the virtual monochromatic X-ray image inferred by the first trained neural network, inputting the first material density image and second material density image into a second trained neural network, the second trained neural network being created by a second neural network performing learning using a plurality of material density images in a training phase, and causing the second trained neural network to infer a third material density image expressing the density of the first reference material and a fourth material density image expressing the density of the second reference material based on the first material density image and second material density image.

Furthermore, aspect 2 of the present invention is CT system for collecting single energy CT data, which includes an X-ray tube in which a prescribed tube voltage is applied, and one or more processors. The one or more processors performs an operation including generating a CT image based on single energy CT data collected from a subject body, inputting the CT image into a first trained neural network, the first trained neural network being created by a first neural network performing learning using a plurality of virtual monochromatic X-ray images in a training phase, causing the first trained neural network to infer a virtual monochromatic X-ray image based on the CT image, generating a first material density image expressing the density of a first reference material and a second material density image expressing the density of a second reference material based on the CT image and the virtual monochromatic X-ray image inferred by the first trained neural network, inputting the first material density image and second material density image into a second trained neural network, the second trained neural network being created by a second neural network performing learning using a plurality of material density images in a training phase, and causing the second trained neural network to infer a third material density image expressing the density of the first reference material and a fourth material density image expressing the density of the second reference material based on the first material density image and second material density image.

Aspect 3 of the present invention is a storage medium, which is one or more non-transitory, computer-readable recording medium in which one or more command executable by one or more processors is stored, wherein the one or more command causes the one or more processors to perform an operation. The operating includes inputting a CT image generated based on single energy CT data collected from a subject body into a first trained neural network, the first trained neural network being created by a first neural network performing learning using a plurality of virtual mono-chromatic X-ray images in a training phase, causing the first trained neural network to infer a virtual monochro-matic X-ray image based on the CT image, generating a first material density image expressing the density of a first reference material and a second material density image expressing the density of a second reference material based on the CT image and the virtual mono-chromatic X-ray image inferred by the first trained neural network, inputting the first material density image and second material density image into a second trained neural network, the second trained neural net-work being created by a second neural network per-forming learning using a plurality of material density images in a training phase, and causing the second trained neural network to infer a third material density image expressing the density of the first reference material and a fourth material density image expressing the density of the second reference material based on the first material density image and second material density image.

Aspect 4 of the present invention is a method of creating a trained neural network, including the steps of creating a first trained neural network, the first trained neural network being created by a first neural network per-forming learning using a first training data set, the first training data set containing a first image set containing a first plurality of virtual monochromatic X-ray images and a second image set containing a second plurality of virtual monochromatic X-ray images, each virtual monochromatic X-ray image of the first plurality of virtual monochromatic X-ray images being a virtual monochromatic X-ray image of a first energy level corresponding to the tube voltage of a CT system that collects single energy CT data, and each virtual mono-chromatic X-ray image of the second plurality of virtual monochromatic X-ray images being a virtual monochromatic X-ray image of a second energy level, and the first neural network performing learning using the first training data set. Each virtual monochromatic X-ray image of the first plurality of virtual monochro-matic X-ray images is used as input of the first neural network and each virtual monochromatic X-ray image of the second plurality of virtual monochromatic X-ray images is output from the first neural network, and creating a second trained neural network, the second trained neural network being created by a second neural network performing learning using a second training data set, the second training data set containing a third image set containing a first plurality of material density images expressing the density of a first reference mate-rial, a fourth image set containing a second plurality of material density images expressing the density of a second reference material, a fifth image set containing a third plurality of material density images expressing the density of the first reference material, and a sixth image set containing a fourth plurality of material density images expressing the density of the second reference material, each virtual monochromatic X-ray image of the first plurality of material density images and each virtual monochromatic X-ray image of the second plurality of material density images being images generated based on a virtual monochromatic X-ray image inferred by the first trained neural net-work, each material density image of the third plurality of material density images and each material density image of the fourth plurality of material density images being images generated by dual energy CT data, and the second neural network performing learning using the first plurality of material density images, second plu-rality of material density images, third plurality of material density images, and fourth plurality of mate-rial density images, such that each material density image of the first plurality of material density images and each material density image of the second plurality of material density images is used as input for the second neural network and each material density image of the third plurality of material density images and each material density image of the fourth plurality of material density images is used as output from the second neural network.

Aspect 5 of the present invention is a device, including one or more processors for performing an operation including inputting a CT image generated based on single energy CT data collected from a subject body into a first trained neural network, the first trained neural network being created by a first neural network performing learning using a plurality of virtual mono-chromatic X-ray images in a training phase, causing the first trained neural network to infer a virtual monochro-matic X-ray image based on the CT image, generating a first material density image expressing the density of a first reference material and a second material density image expressing the density of a second reference material based on the CT image and the virtual mono-chromatic X-ray image inferred by the first trained neural network, inputting the first material density image into a third trained neural network, the third trained neural network being created by the third trained neural network performing learning using a plurality of material density images expressing the density of the first reference material in a training phase, causing the third trained neural network to infer a third material density image expressing the density of the first reference material based on the first material density image, inputting the second material density image into a fourth trained neural network, the fourth trained neural network being created by the fourth neural network performing learning using a plurality of material density images expressing the density of the second reference material in a training phase, and causing the fourth trained neural network to infer a fourth material density image expressing the density of the second reference material based on the second material density image.

A first trained neural network is created by a first neural network performing learning using a plurality of virtual monochromatic X-ray images. Thus, the first trained neural network is configured to perform inference processing in a CT value domain. Furthermore, the virtual monochromatic X-ray image is inferred by inputting a CT image into the first trained neural network. Next, a first material density image expressing the density of a first reference material and a second material density image expressing the density of a second reference material are generated based on the CT image and the inferred virtual monochromatic X-ray image. However, the virtual monochromatic X-ray images used to calculate the first and second material density images are inferred from a CT image generated based on single energy CT data. In general, a virtual monochromatic X-ray image inferred based on single energy CT data is somewhat less accurate in terms of CT values than a virtual monochromatic X-ray image calculated based on dual energy CT data. Therefore, the accuracy of the first and second material density images calculated based on the CT image and the inferred virtual monochromatic X-ray image is limited.

Thus, in Aspects 1 to 3, in addition to the first trained neural network, a second trained neural network is created, which performs inference processing in the density domain. The second trained neural network performs inference processing in the density domain. Therefore, when the first and second material density images generated based on single energy CT data are input to the second trained neural network, inference processing is performed in the density domain. Thus, by inputting the first and second material density images into the second trained neural network, it is possible to infer third and fourth material density images that are more reliable than the first and second material density images in terms of calculated densities of reference materials. Therefore, it is possible to bring the third and fourth material density images closer to the accuracy of the material density images calculated from dual energy CT data.

Aspect 4 provides a method of creating the first and second trained neural networks used in Aspects 1 to 3. Aspect 5 describes an example of using a third trained neural network for inferring a third material density image based on a first material density image and a fourth trained neural network for inferring a fourth material density image based on a second material density image. In Aspect 5, the third and fourth trained neural networks perform inference processing in the density domain. Therefore, it is possible to infer third and fourth material density images that are more reliable than the first and second material density images in terms of calculated density of reference materials.

BRIEF DESCRIPTION OF DRAWINGS

FIG. 12 is an explanatory diagram of a scan of a subject body; and

DETAILED DESCRIPTION

An embodiment for carrying out the invention will be described below, but the present invention is not limited to the following embodiment.

Figure 1:
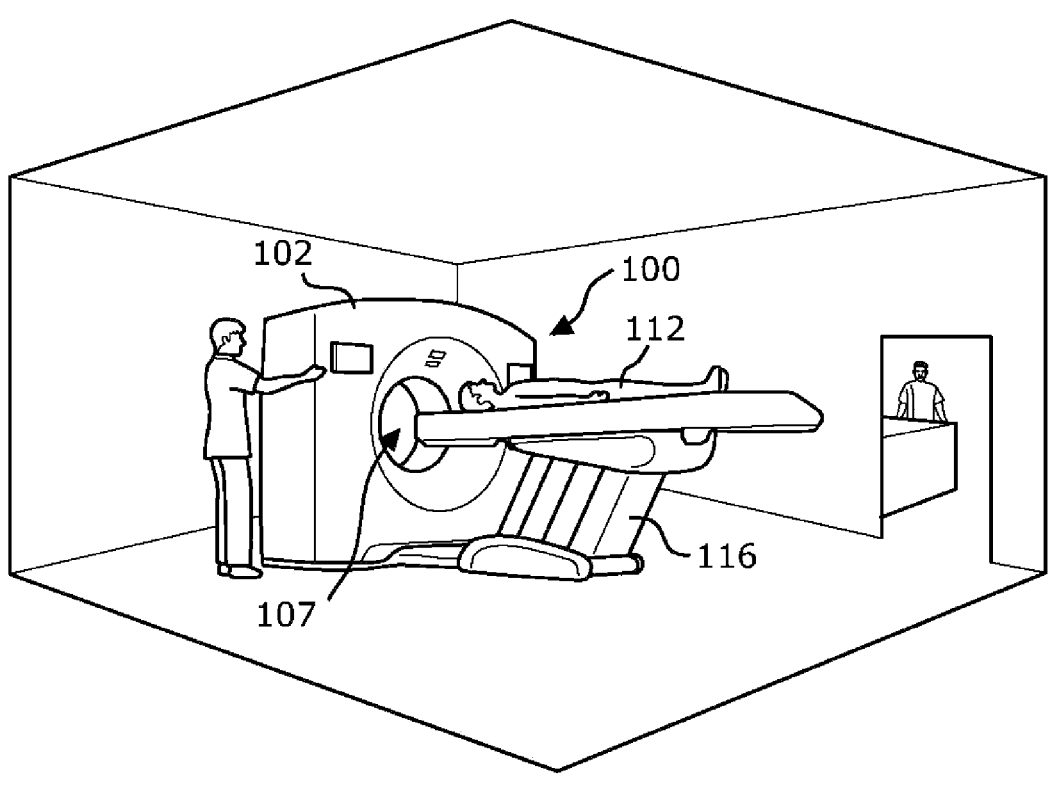
FIG. 1 is a perspective view of the CT system 100 of the present embodiment.

FIG. 1 is a perspective view of a CT system 100 of the present embodiment. The CT system 100 has a gantry 102. The gantry 102 has an opening 107, a subject body 112 is transported through the opening 107, and a scan of subject body 112 is performed.

Figure 2:
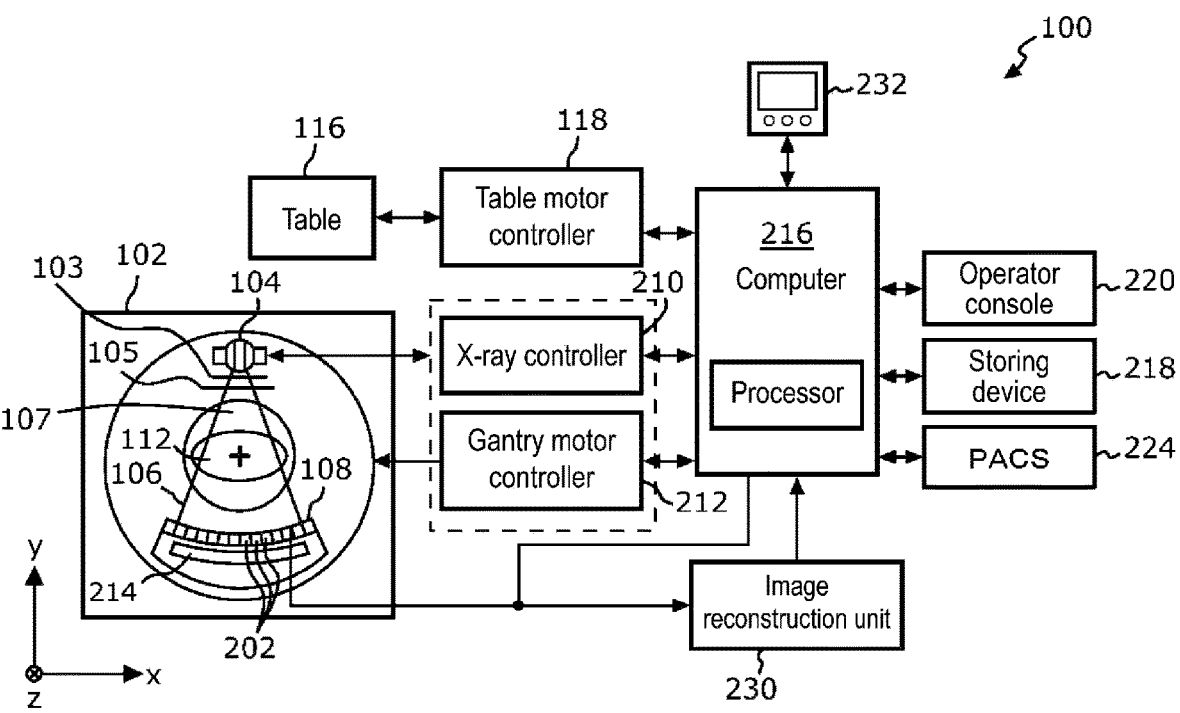
FIG. 2 is a block diagram of the CT system 100.

FIG. 2 is a block diagram of the CT system 100. The gantry 102 is equipped with an X-ray tube 104, a filter part 103, a front collimator 105, and a detector array 108. The X-ray tube 104 generates X-rays when a prescribed voltage (e.g., 120 kVp) is applied to the cathode-anode tube. The filter part 103 includes, for example, a flat plate filter and/or a bow-tie filter. The front collimator 105 is a component that narrows the X-ray irradiation range so that X-rays are not emitted in unwanted areas.

The detector array 108 includes a plurality of detector elements 202. A plurality of detector elements 202 detect the X-ray beam 106 that is emitted from the X-ray tube 104 and passes through the subject body 112 serving as an imaging target. Thus, the detector array 108 can acquire projection data for each view.

The projection data detected by an X-ray detector 108 is collected by a DAS (Data Acquisition System) 214. The DAS 214 performs prescribed processing, including sampling and digital conversion, on the collected projection data. The processed projection data is transmitted to a computer 216. The computer 216 stores the data from the DAS 214 in a storage device 218. The storage device 218 includes one or more storage media that store programs and instructions to be executed by the processor. The storage medium can be, for example, one or more non-transitory, computer-readable storage media. Storage devices 218 may include, for example, hard disk drives, floppy disk drives, compact disc read/write (CD-R/W) drives, digital versatile disk (DVD) drives, flash drives, and/or solid state storage drives.

The computer 216 includes one or a plurality of processors. The computer 216 uses one or a plurality of processors to output commands and parameters to the DAS 214, X-ray controller 210, and/or gantry motor controller 212, to control a system operation such as data acquisition and/or data processing.

An operator console 220 is linked to the computer 216. An operator can enter prescribed operator inputs related to the operation of the CT system 100 into the computer 216 by operating the operator console 220. The computer 216 receives operator input, including commands and/or scan parameters, via the operator console 220 and controls system operation based on that operator input. The operator console 220 can include a keyboard (not shown) or touch screen for the operator to specify commands and/or scan parameters.

The X-ray controller 210 controls the X-ray tube 104 based on a signal from the computer 216. In addition, the gantry motor controller 212 controls the gantry motor based on a signal from the computer 216.

FIG. 2 illustrates only one operator console 220, but two or more operator consoles may be linked to the computer 216. In addition, the CT system 100 may also allow a plurality of remotely located displays, printers, workstations and other devices to be coupled via, for example, wired and/or wireless networks. In one embodiment, for example, the CT system 100 may include or be linked to a Picture Archiving and Communication System (PACS) 224. In a typical implementation, a PACS 224 can be coupled to a remote system such as a radiology department information system, hospital information system, and/or internal or external network (not depicted).

The computer 216 supplies commands to the table motor controller 118 to control the table 116. The table motor controller 118 can control the table 116 based on commands received. In particular, the table motor controller 118 can move the table 116 so that the subject body 112 is properly positioned within the opening 107 of the gantry 102.

As mentioned above, the DAS 214 samples and digitally converts the projection data acquired by the detector elements 202. The image reconstruction unit 230 then reconstructs the image using the sampled and digitally converted data. The image reconstruction unit 230 includes one or a plurality of processors, which can perform the image reconstruction process. In FIG. 2, the image reconstruction unit 230 is illustrated as a separate structural element from the computer 216, but the image reconstruction unit 230 may form a part of the computer 216. In addition, the computer 216 may also perform one or more functions of the image reconstruction unit 230. In addition, the image reconstructor 230 may be located away from the CT system 100 and operatively connected to the CT system 100 using a wired or wireless network.

The image reconstruction unit 230 can store the reconstructed image in the storage device 218. The image reconstruction unit 230 may also transmit the reconstructed image to the computer 216. The computer 216 can transmit the reconstructed image and/or patient information to a display part 232 communicatively coupled to the computer 216 and/or image reconstructor 230.

The computer 216 and/or image reconstructor 230 forms a device that performs processing of data collected by scanning the subject body, a device that performs various processes based on data received from the operator console 220, and a device that performs various processes based on data received from various controllers (118, 210, 212, and the like).

Note that at least some of the processing performed by the computer 216 and/or image reconstructor 230 may be performed by an external device that is separate from the CT system 100.

The various methods and processes described in the present specification can be stored as executable instructions on a non-transitory storage medium within the CT system 100. The executable instructions may be stored on a single storage medium or distributed across multiple storage mediums. One or more processors provided in the CT system 100 execute the various methods, steps, and processes described in the present specifications in accordance with instructions stored on a storage medium.

The CT system 100 is configured as described above.

The CT system 100 of the present embodiment is a system that performs single energy CT imaging, but is configured to acquire a high-quality material density image.

A basic concept of a technique for acquiring a material density image using a CT system that performs single energy CT imaging is described below, with reference to FIG. 3.

Figure 3:
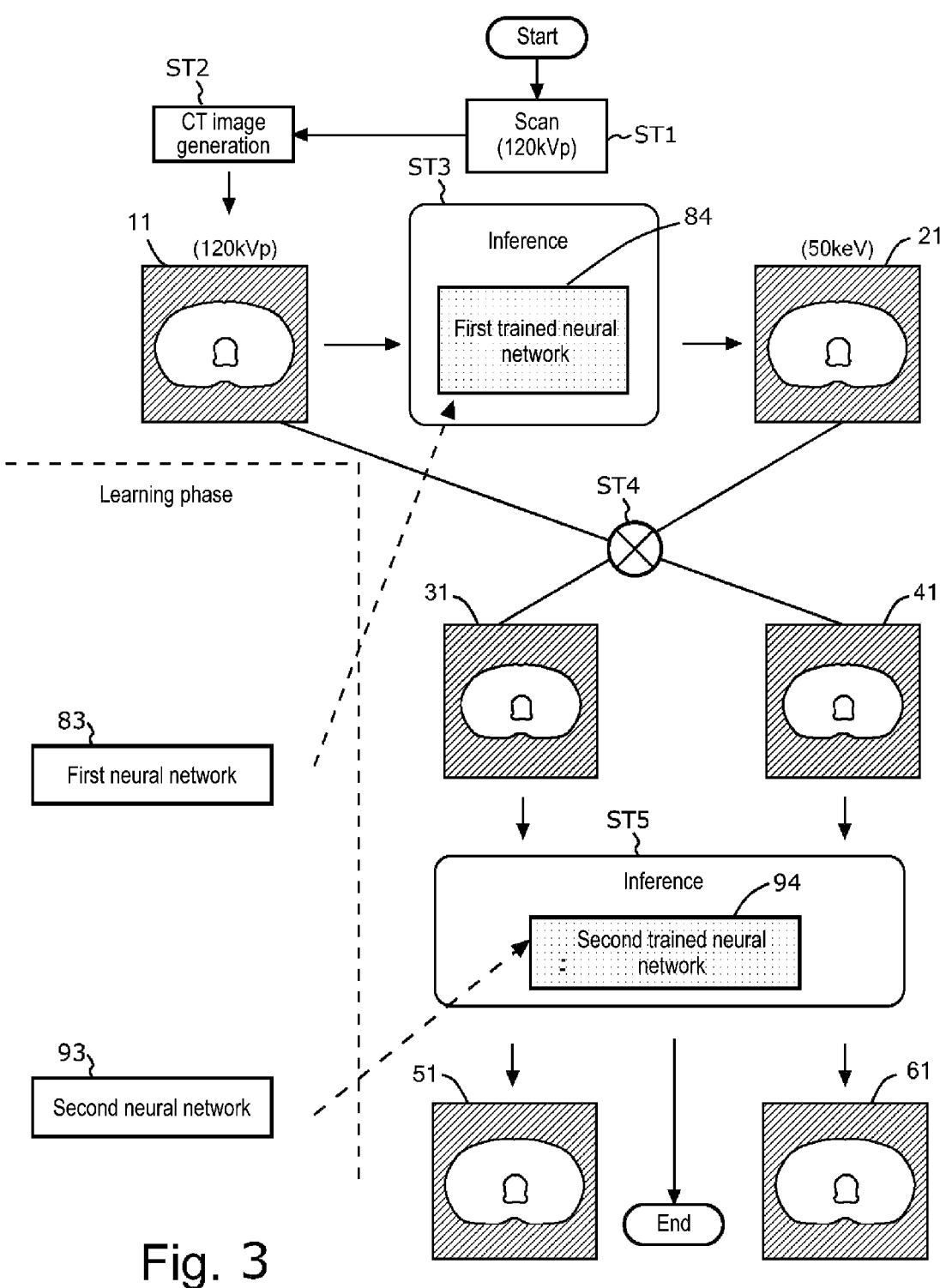
FIG. 3 is a flowchart describing a basic concept for acquiring a material density image in the present embodiment.

FIG. 3 is a flowchart describing the basic concept for acquiring a material density image in the present embodiment.

In step ST1, the subject body is scanned using the CT system 100 that performs single energy CT imaging. In the present embodiment, the tube voltage of the CT system is 120 kVp, but another tube voltage may be used.

In step ST2, a CT image 11 is generated based on data acquired by scanning the subject body.

In step ST3, the CT image 11 obtained in step ST2 is input to a first trained neural network 84. Furthermore, the first trained neural network 84 infers a virtual monochromatic X-ray image 21 based on the input CT image 11.

Note that the first trained neural network 84 is generated by a first neural network 83 performing learning using a plurality of virtual monochromatic X-ray images in a training phase. An example of a specific method of creating the first trained neural network 84 will be described later.

The tube voltage of 120 (kVp) of the CT system 100 corresponds to an energy level of approximately 70 (keV). Therefore, when considered from the perspective of energy level, the CT image 11 corresponds to a virtual monochromatic X-ray image of 70 (keV). Furthermore, the first trained neural network 84 infers the virtual monochromatic X-ray image 21 having a different energy level from 70 (keV) based on the CT image 11. FIG. 3 depicts an example of inferring a virtual monochromatic X-ray image of 50 (keV) as an example of the virtual monochromatic X-ray image 21. After inferring the virtual monochromatic X-ray image 21, the flow proceeds to step ST4.

In step ST4, a first material density image 31 and a second material density image 41 are generated based on the CT image 11 used as input for the first trained neural network 84 and the virtual monochromatic X-ray image 21 of 50 (keV) inferred by the first trained neural network 84. The first material density image 31 is an image expressing the density of the first reference material, and the second material density image 41 is an image representing the density of the second reference material. The first and second reference materials can be determined based on materials included in an imaging site of the subject body. Two reference materials are preferably chosen to have significantly different effective atomic numbers. For example, water and iodine can be selected as the two reference materials.

In step ST5, the pair of the first material density image 31 and second material density image 41 generated in step ST4 are input to a second trained neural network 94. Furthermore, the second trained neural network 94 infers a pair of a third material density image 51 expressing the density of the first reference material and a fourth material density image 61 expressing the density of the second reference material based on the input pair of the first material density image 31 and second material density image 41. Note that the second trained neural network 94 is generated by a second neural network 93 performing learning using a plurality of material density images in a training phase. An example of a specific method of creating the second trained neural network 94 will be described later. Therefore, in the present embodiment, the material density images 51 and 61 are inferred using the first and second trained neural networks 84 and 94.

The first trained neural network 84 is created by the first neural network 83 performing learning using a plurality of virtual monochromatic X-ray images. Thus, the first trained neural network 84 is configured to perform inference processing in a CT value domain. Furthermore, the CT image 11 is input to the first trained neural network 84 to infer the virtual monochromatic X-ray image 21. The CT image 11 corresponds to a virtual monochromatic X-ray image of 70 (keV), and the virtual monochromatic X-ray image 21 inferred by the first trained neural network 84 is a virtual monochromatic X-ray image of 50 (keV). Therefore, the CT image 11 and virtual monochromatic X-ray image 21 are images having mutually different energy levels. The first material density image 31 and second material density image 41 can be generated by performing material discrimination processing using the CT image 11 and virtual monochromatic X-ray image 21. The first material density image 31 is, for example, a water density image, and the second material density image 41 is, for example, an iodine density image. Therefore, by performing step ST4, the two material density images 31 and 41 can be generated.

However, the virtual monochromatic X-ray images 21 used to calculate the first and second material density images 31 and 41 are inferred from the CT image 11 generated based on single energy CT data. In general, a virtual monochromatic X-ray image inferred based on single energy CT data is somewhat less accurate in terms of CT values than a virtual monochromatic X-ray image calculated based on dual energy CT data. Therefore, if the material density images 31 and 41 are calculated based on the CT image 11 and the virtual monochromatic X-ray image 21, the accuracy of the material density images 31 and 41 is also limited.

Thus, in the present embodiment, in addition to the first trained neural network 84, a second trained neural network 94 is created, which performs inference processing in the density domain. The second trained neural network 94 performs inference processing in the density domain. Therefore, when the material density images 31 and 41 generated based on single energy CT data are input to the second trained neural network 94, inference processing is performed in the density domain, and material density images 51 and 61 are output. Therefore, the second trained neural network 94 is able to infer the material density images 51 and 61 that are more reliable than the input material density images 31 and 41 in terms of the density values of the reference materials.

Figure 4:
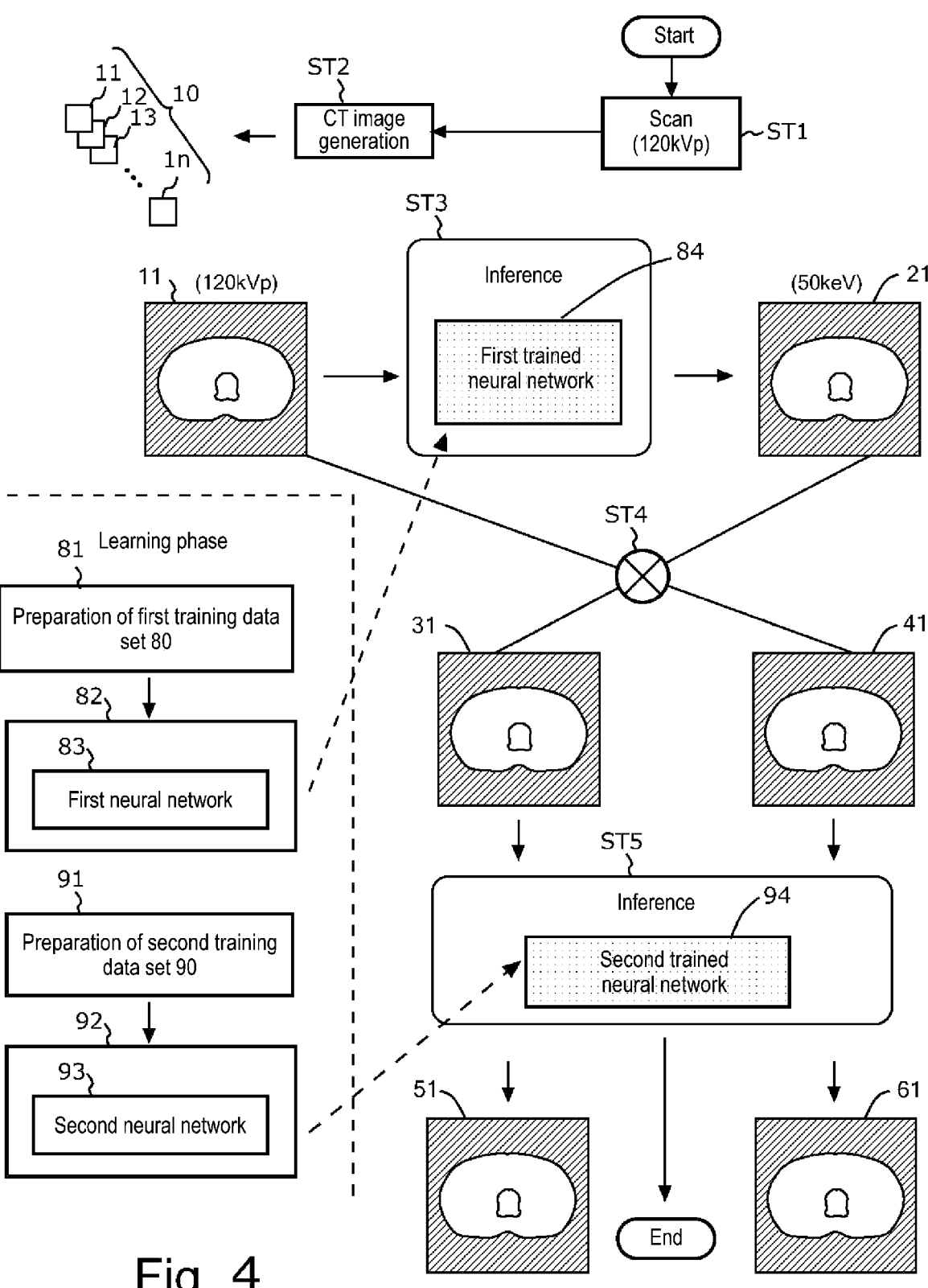
FIG. 4 is a diagram depicting a flow for inferring a material density image in the present embodiment.

The inventors of the present application considered inferring the material density images 51 and 61 in accordance with the principle above. A flow for inferring the material density images 51 and 61 in accordance with the principle above is described below. FIG. 4 is a diagram depicting the flow for inferring a material density image in the present embodiment. Note that in the present embodiment as described with reference to FIG. 3, the two trained neural networks 84 and 94 are used to infer the material density images 51 and 61; therefore, the two trained neural networks 84 and 94 must be prepared in advance. Thus, the following describes the training phase in which the two trained neural networks 84 and 94 are created. Furthermore, after describing a training phase, a flow for inferring the material density images 51 and 61 in accordance with the principle above will be described.

In a training phase, the first trained neural network 84 and second trained neural network 94 are created. A method of creating the first trained neural network 84 will first be described below, followed by a method of creating the second trained neural network 94.

Figure 5:
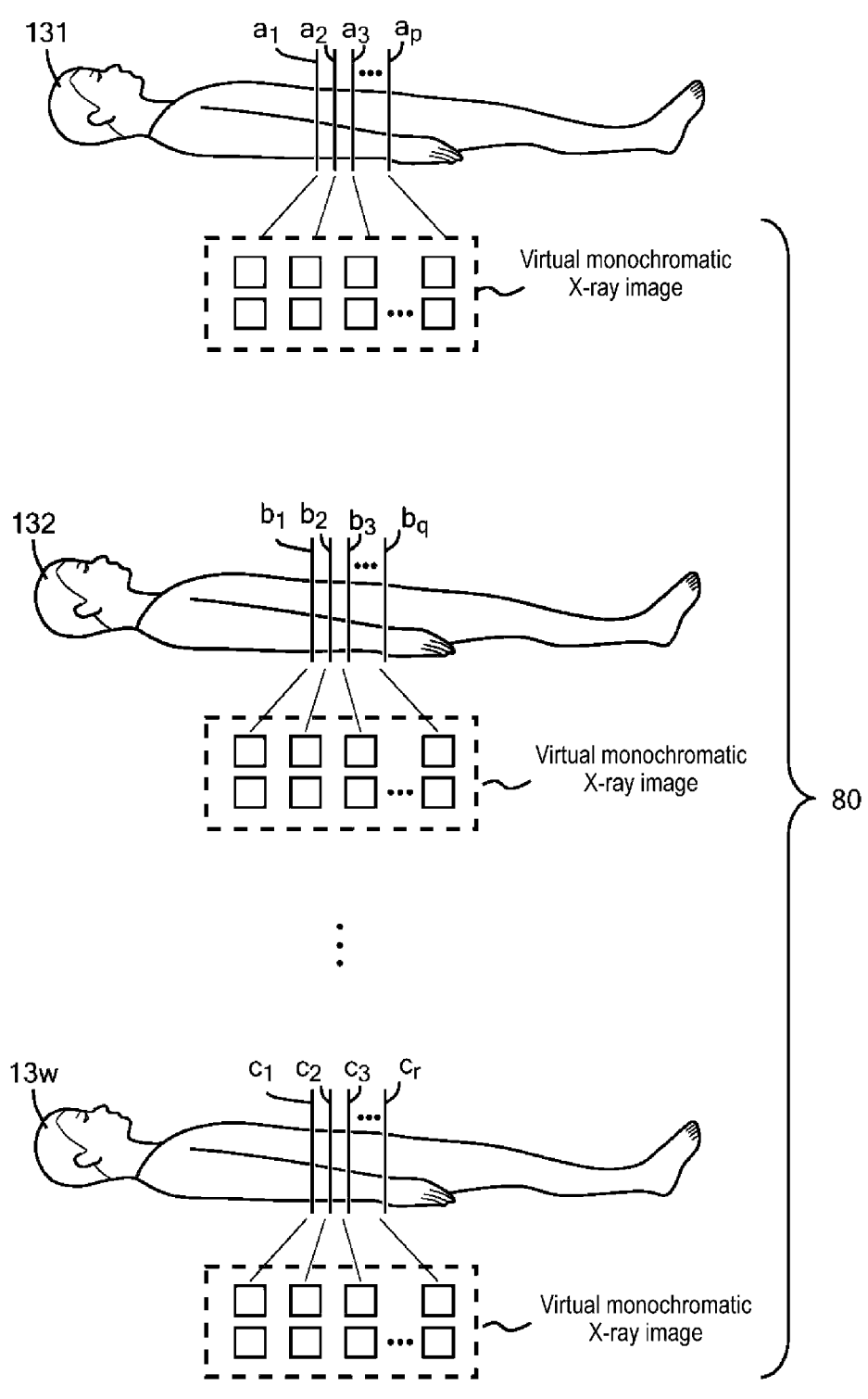
FIG. 5 is an explanatory diagram of a first training data set 80.
Figure 6:
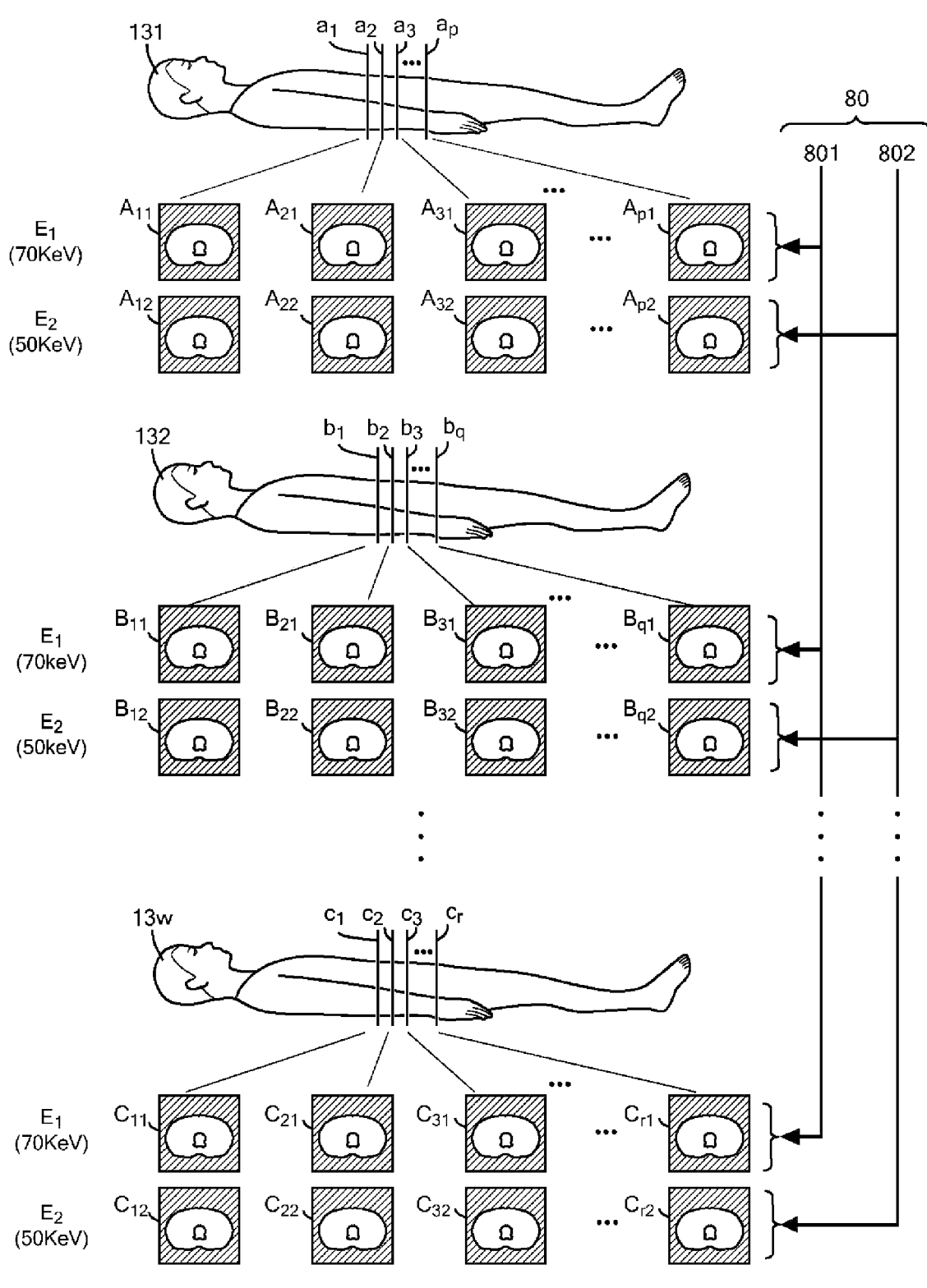
FIG. 6 is an explanatory diagram of virtual monochromatic X-ray images acquired from patients 131 to 13$w$.
Figure 7:
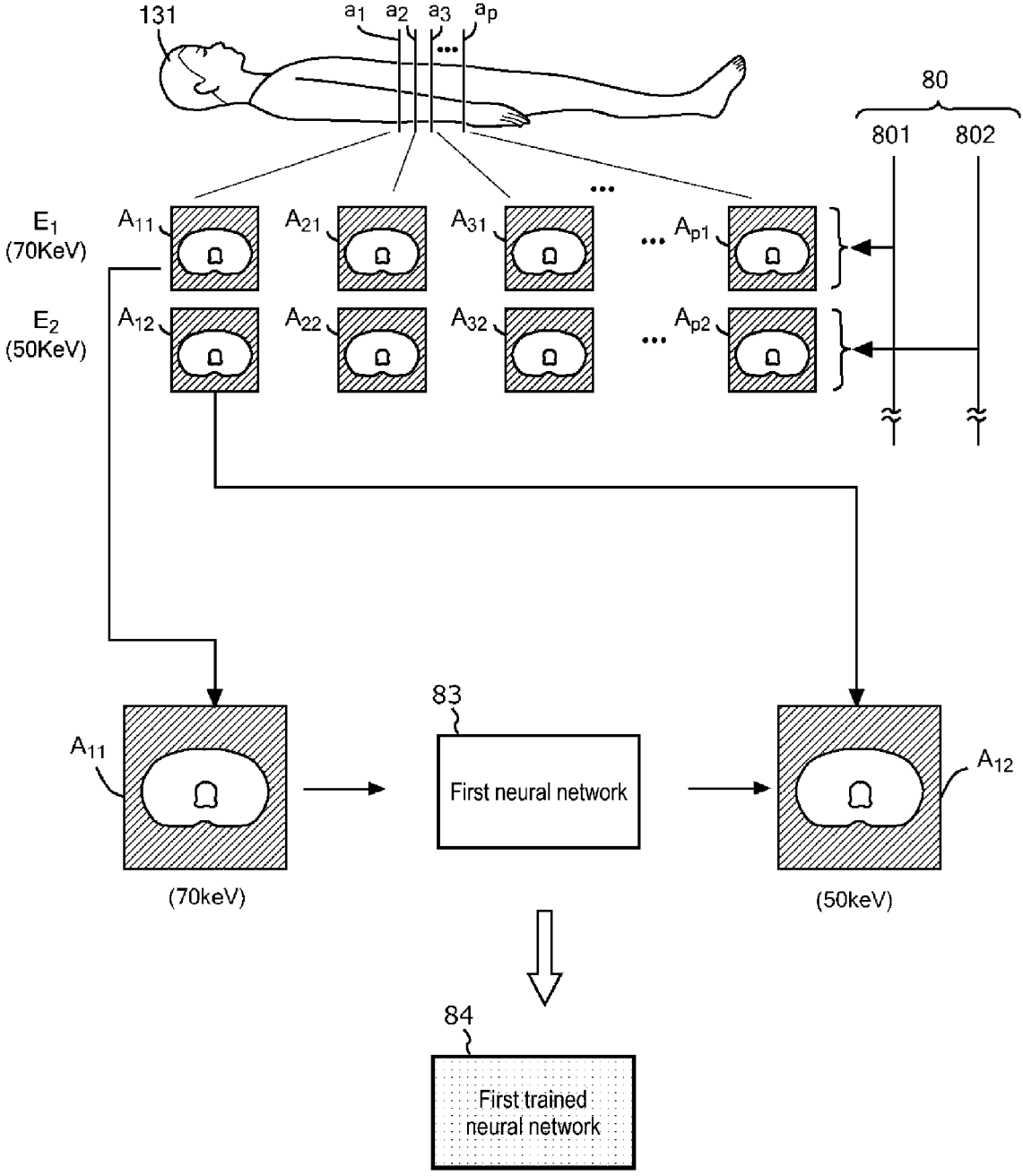
FIG. 7 is an explanatory diagram of a training method of a first neural network 83.

FIGS. 5 to 7 are explanatory diagrams of the method of creating the first trained neural network 84. First, in step ST81 (see FIG. 4), a first training data set 80 necessary for creating the first trained neural network 84 is prepared.

FIG. 5 is an explanatory diagram of the first training data set 80. The first training data set 80 can be obtained from hospitals and other medical institutions. For example, virtual monochromatic X-ray images acquired by actually contrast-enhanced CT scanning a plurality of patients 131 to 13$w$ at a medical institution can be prepared as training data. These virtual monochromatic X-ray images are generated based on dual energy CT data.

FIG. 6 is an explanatory diagram of virtual monochromatic X-ray images acquired from the patients 131 to 13$w$. Although the virtual monochromatic X-ray images obtained from the patient 131 to 13$w$ include virtual monochromatic X-ray images acquired at various time phases, for the sake of explanation, a virtual monochromatic X-ray image of 70 (keV) and a virtual monochromatic X-ray image of 50 (keV) acquired at a prescribed time phase (e.g., arterial phase) are considered as virtual monochromatic X-ray images obtained from the patient 131 to 13$w$. However, it should be noted that the present invention may use images from various time phases as training data.

First, the patient 131 is described. Virtual monochromatic X-ray images $A_{11}$ to $A_{p2}$ are acquired from the patient 131. Referring to slice $a_1$ of the patient 131, two of the virtual monochromatic X-ray images $A_{11}$ and $A_{12}$ are acquired in the slice $a_1$. The virtual monochromatic X-ray images $A_{11}$ and $A_{12}$ are generated based on dual energy CT data and are virtual monochromatic X-ray images having mutually different energy levels. The virtual monochromatic X-ray image $A_{11}$ is a virtual monochromatic X-ray image at energy level E1 (=70 (keV)), and the virtual monochromatic X-ray image $A_{12}$ is at energy level E2 (=50 (keV)).

Furthermore, referring to a slice $a_2$, two virtual monochromatic X-ray images $A_{21}$ and $A_{22}$ are acquired in the slice $a_2$. The virtual monochromatic X-ray images $A_{21}$ and $A_{22}$ are generated based on dual energy CT data and are virtual monochromatic X-ray images having mutually different energy levels. The virtual monochromatic X-ray image $A_{21}$ is a virtual monochromatic X-ray image at energy level E1 (=70 (keV)), and the virtual monochromatic X-ray image $A_{22}$ is at energy level E2 (=50 (keV)).

Similarly below, virtual monochromatic X-ray images having the energy levels E1 (=70 (keV)) and E2 (=50 (keV)) are acquired in the other slices $a_3$ to $a_p$. Therefore, the virtual monochromatic X-ray images $A_{11}$ to $A_{p1}$ having the energy level E1 (=70 (keV)) and $A_{12}$ to $A_{p2}$ having the energy level E2 (=50 (keV)) are acquired from the patient 131.

Furthermore, for the other patients 132 to 13$w$, the virtual monochromatic X-ray images having the energy levels E1 (=70 (keV)) and E2 (=50 (keV)) are acquired for each slice, as for the patient 131. For example, the virtual monochromatic X-ray images $B_{11}$ to $B_{q1}$ having the energy level E1 (=70 (keV)) and $B_{12}$ to $B_{q2}$ having the energy level E2 (=50 (keV)) are acquired from the patient 132. Furthermore, the virtual monochromatic X-ray images $C_{11}$ to $C_{r1}$ having the energy level E1 (=70 (keV)) and $C_{12}$ to $C_{r2}$ having the energy level E2 (=50 (keV)) are acquired from the patient 13$w$.

Therefore, the first training data set 80 contains a first image set 801 containing the plurality of virtual monochromatic X-ray images of 70 (keV) and a second image set 802 containing the plurality of virtual monochromatic X-ray images of 50 (keV). Note that the energy levels of the virtual monochromatic X-ray image are not limited to 70 (keV) and 50 (keV), but may be energy levels other than 70 (keV) and 50 (keV). Furthermore, the example above describes a case in which actual virtual monochromatic X-ray images acquired from the patients 131 to 13$w$ are used as training data. However, prescribed pre-processing may be performed on the actual virtual monochromatic X-ray images acquired from the patients 131 to 13$w$, and the virtual monochromatic X-ray images after pre-processing has been performed may be used as training data. After preparing the first training data set 80, the flow proceeds to step ST82 (see FIG. 4).

In step ST82, the first neural network 83 performs learning using the first training data set 80, thereby creating the first trained neural network 84. The following describes a training method of the first neural network 83.

FIG. 7 is an explanatory diagram of the training method of the first neural network 83. As described earlier, the first training data set 80 contains the first image set 801 containing the virtual monochromatic X-ray images $A_{11}$ to $A_{r1}$ of 70 (keV) and the second image set 802 containing the monochromatic X-ray images $A_{12}$ to $A_{r2}$ of 50 (keV). Note that due to page layout limitations, FIG. 7 depicts the virtual monochromatic X-ray images $A_{11}$ to $A_{p1}$ obtained from the patient 131 of the first image set 801 and the virtual monochromatic X-ray images $A_{12}$ to $A_{p2}$ obtained from the patient 131 of the second image set 802.

First, training is performed using the virtual monochromatic X-ray images $A_{11}$ and $A_{12}$ obtained from the slice $a_1$ of the patient 131. Specifically, the neural network 83 performs learning using the virtual monochromatic X-ray images $A_{11}$ and $A_{12}$, such that the virtual monochromatic X-ray image $A_{11}$ of 70 (keV) is used as input to the neural network 83 and the virtual monochromatic X-ray image $A_{12}$ of 50 (keV) is output from the neural network 83. Note that the reason for using the virtual monochromatic X-ray image of 70 (keV) as input to the neural network 83 is that the energy level of 70 (keV) corresponds to the energy level of the tube voltage (120 kVp) of the CT system 100 used to actually scan the subject body 112.

Note that although FIG. 7 depicts a case in which the neural network 83 performs learning using the virtual monochromatic X-ray images $A_{11}$ and $A_{12}$ of slice $a_1$, virtual monochromatic X-ray images of the other slices $a_2$ to $a_p$ are also used for training of the neural network 83 in the same manner as the virtual monochromatic X-ray images $A_{11}$ and $A_{12}$ of slice $a_1$.

Furthermore, the virtual monochromatic X-ray images of each slice of the other patients 132 to 13$w$ (see FIG. 6) are also used to train the neural network 83 in the same manner as the virtual monochromatic images of patient 131.

Therefore, training using the first training data set 80 is performed, such that the virtual monochromatic X-ray images of 70 (keV) of the first image set 801 are used as input to the neural network 83, and the virtual monochromatic X-ray images of 50 (keV) of the second image set 802 are output from the neural network 83.

Thus, the neural network 83 performs learning using the first training data set 80, creating the first trained neural network 84. Note that in the training phase, a prescribed range of CT values may be intensively learned. For example, in a scan using a contrast agent, the CT value of the contrast agent is important for diagnosis; therefore, the range of CT values of the contrast agent may be intensively learned. By determining the range of CT values to be intensively learned in this manner, it is possible to provide a trained neural network that can infer an image that is even more suitable for diagnostic purposes. The trained neural network 84 is stored in the storage device 218 (see FIG. 2) of the CT system 100. Note that the trained neural network 84 may be stored on an external storage device accessible by the CT system 100.

Next, the method of creating the second trained neural network 94 is described.

Figure 8:
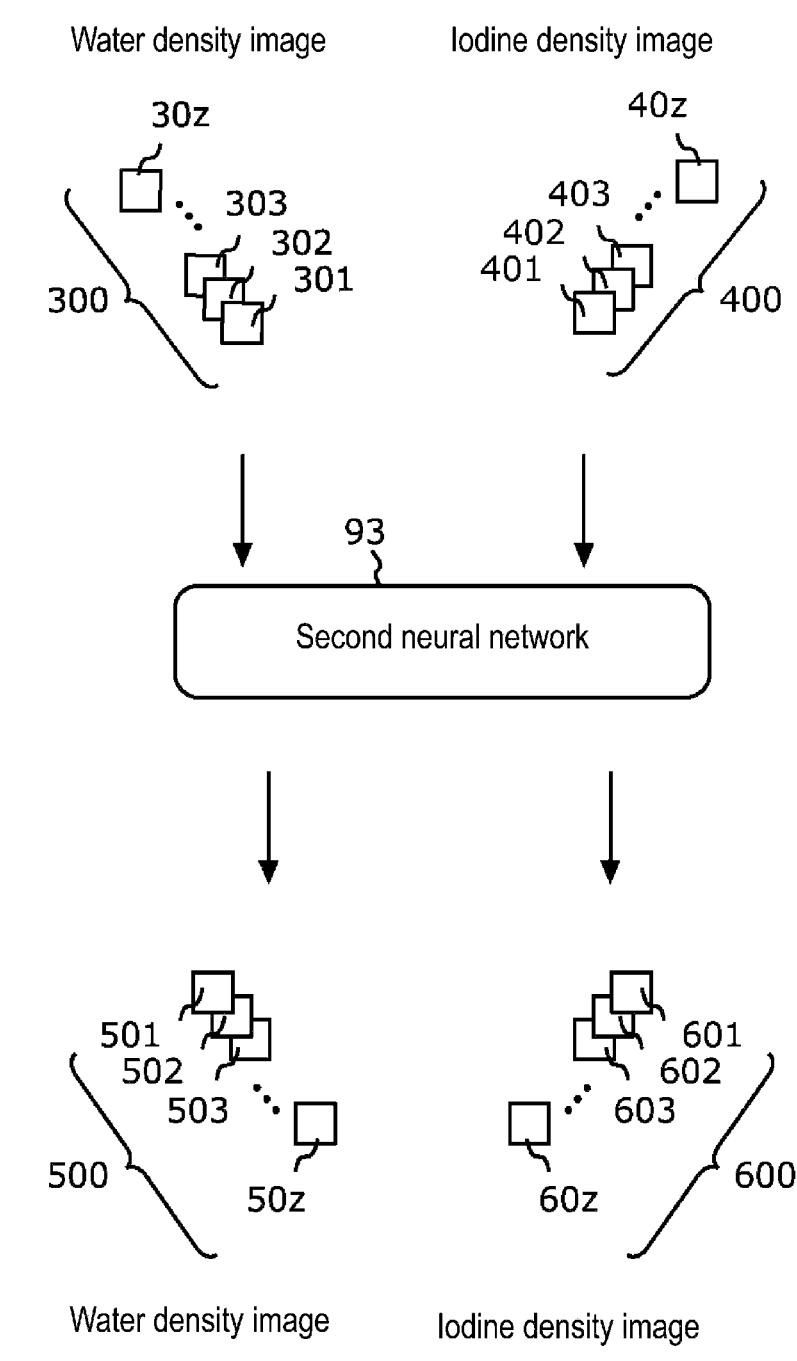
FIG. 8 is an explanatory diagram of a second training data set 90.
Figure 9:
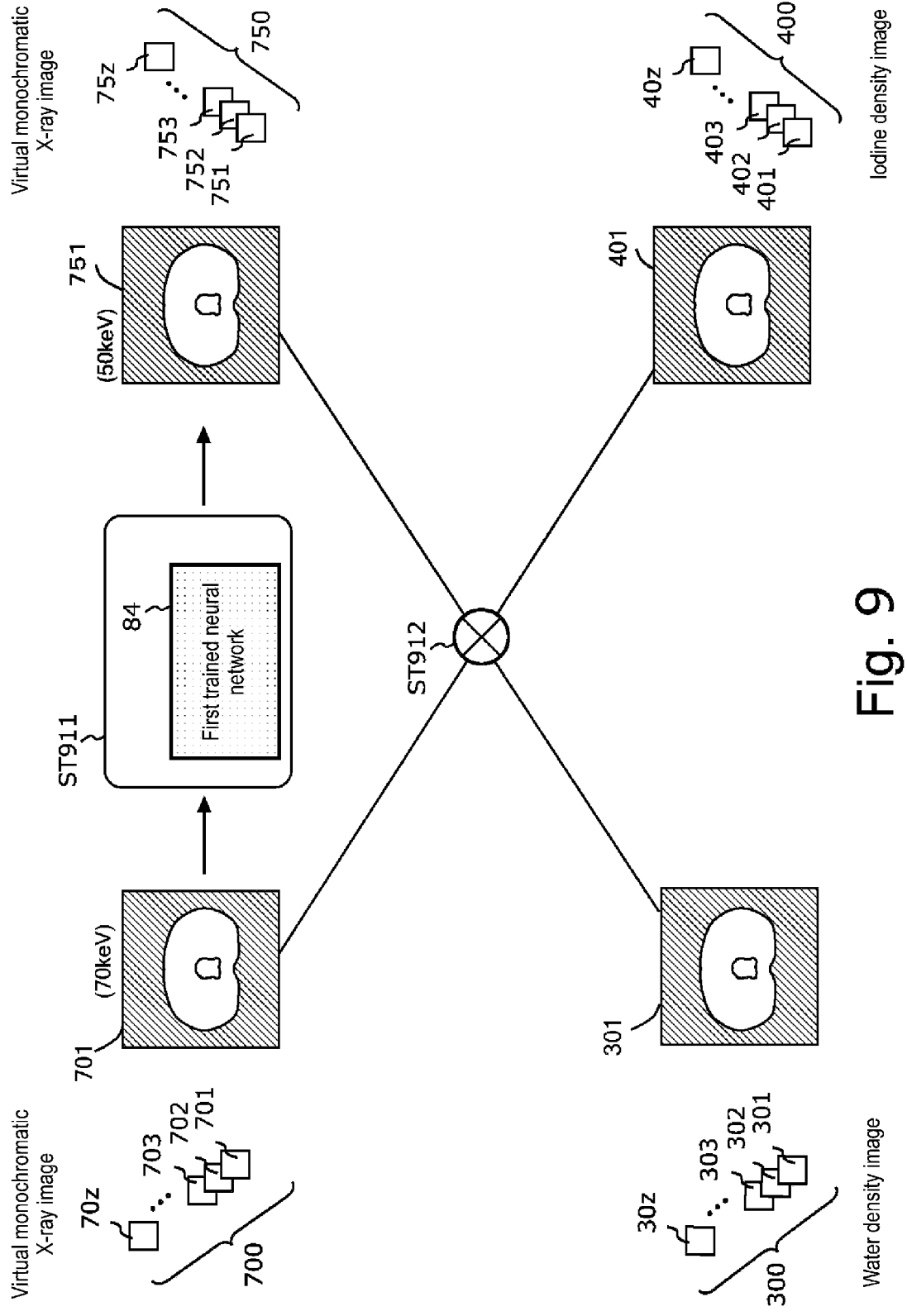
FIG. 9 is an explanatory diagram of a method of preparing image sets 300 and 400.
Figure 10:
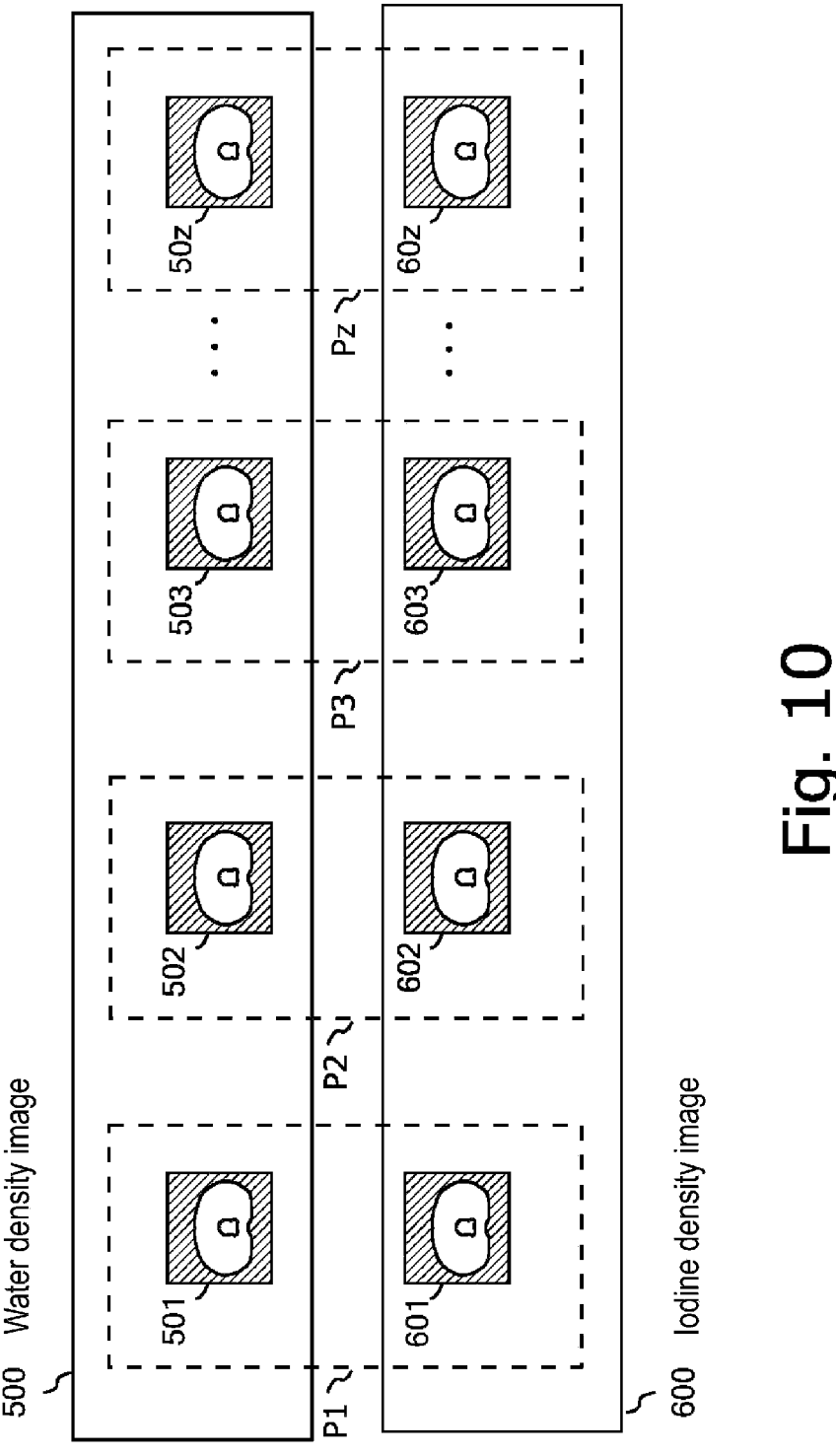
FIG. 10 is an explanatory diagram of image sets 500 and 600.

FIGS. 8 to 10 are explanatory diagrams of the method of creating the second trained neural network 94. First, in step ST91 (see FIG. 4), a second training data set 90 necessary for creating the second trained neural network 94 is prepared.

FIG. 8 is an explanatory diagram of the second training data set 90. The second training data set 90 contains a third image set 300, a fourth image set 400, a fifth image set 500, and a sixth image set 600. The image set 300 contains a first plurality of material density images 301 to 30$z$, and the image set 400 contains a second plurality of material density images 401 to 40$z$. The image set 500 contains a third plurality of material density images 501 to 50$z$, and the image set 600 contains a fourth plurality of material density images 601 to 60$z$. The first plurality of material density images 301 to 30$z$ and the third plurality of material density images 501 to 50$z$ are images expressing the density of the first reference material. On the other hand, the second plurality of material density images 401 to 40$z$ and the fourth plurality of material density images 601 to 60$z$ are images expressing the density of the second reference material. The first and second reference materials can be determined based on materials included in an imaging site of the subject body. Two reference materials are preferably chosen to have significantly different effective atomic numbers. For example, water and iodine can be selected as the two reference materials. For the sake of explanation, an example shall be considered below in which the first reference material is water, and the second reference material is iodine. Therefore, the description below will continue with the assumption that the material density images 301 to 30$z$ in the image set 300 are water density images 301 to 30$z$ and the material density images 401 to 40$z$ in the image set 400 are iodine density images 401 to 40$z$. Furthermore, similarly, the description will continue with the assumption that the material density images 501 to 50$z$ in the image set 500 are water density images 501 to 50$z$ and the material density images 601 to 60$z$ in the image set 600 are iodine density images 601 to 60$z$.

The water density images 301 to 30$z$ in the image set 300 and the iodine density images 401 to 40$z$ in the image set 400 are used as data input to the second neural network 93. On the other hand, the water density images 501 to 50$z$ in the image set 500 and the iodine density images 601 to 60$z$ in the image set 600 are used as correct data with respect to the output of the second neural network 93.

A method of preparing these image sets is described below. FIG. 9 is an explanatory diagram of the method of preparing the image sets 300 and 400. The image sets 300 and 400 are generated using the previously created first trained neural network 84. First, an input image set 700 to be input to the first trained neural network 84 is prepared.

The input image set 700 includes virtual monochromatic X-ray images 701 to 70$z$. These virtual monochromatic X-ray images can be obtained from a hospital or other medical institution. For example, a plurality of virtual monochromatic X-ray images acquired by actually scanning a plurality of the patients at a medical institution can be prepared as the virtual monochromatic X-ray images 701 to 70$z$. The virtual monochromatic X-ray images 701 to 70$z$ are the same virtual monochromatic X-ray images of 70 (keV) that were used as input to the first neural network 83 (e.g., see FIG. 7) when creating the first trained neural network 84. After preparing the input image set 700 of the virtual monochromatic X-ray images 701 to 70$z$, the flow proceeds to step ST911.

In step ST911, each virtual monochromatic x-ray image of the input image set 700 is input to the first trained neural network 84. FIG. 9 depicts an example of the input image set 700 in which the virtual monochromatic X-ray image 701 of 70 (keV) is input to the first trained neural network 84. The first trained neural network 84 infers a virtual monochromatic X-ray image 751 of 50 (keV) when the virtual monochromatic X-ray image 701 of 70 (keV) is input.

In the same manner below, the other virtual monochromatic X-ray images 702-70$z$ of the input image set 700 are input to the first trained neural network 84, and virtual monochromatic X-ray images of 50 (keV) corresponding to each input virtual monochromatic X-ray image are inferred.

Therefore, by inputting the virtual monochromatic X-ray images 701 to 70$z$ of 70 (keV) of the input image set 700 into the first trained neural network 84, an output image set 750 containing virtual monochromatic X-ray images 751 to 75$z$ of 50 (keV) can be inferred. After inferring the output image set 750, the flow proceeds to step ST912.

In step ST912, the image set 300 containing the water density images 301 to 30$z$ and the image set 400 containing the iodine density images 401 to 40$z$ are generated based on the input image set 700 containing the virtual monochromatic X-ray images 701 to 70$z$ of 70 (keV) and the output image set 750 containing the inferred virtual monochromatic X-ray images 751 to 75$z$ of 50 (keV).

When generating the image sets 300 and 400, one virtual monochromatic X-ray image 701 from the input image set 700 is first selected. Next, from the output image set 750, the virtual monochromatic X-ray image 751 is selected, which is inferred based on the virtual monochromatic X-ray image 701. Furthermore, the water density image 301 and iodine density image 401 are generated based on the virtual monochromatic X-ray image 701 and the virtual monochromatic X-ray image 751.

The virtual monochromatic X-ray image 701 is a virtual monochromatic X-ray image of 70 (keV), and virtual monochromatic X-ray image 751 is a virtual monochromatic X-ray image of 50 (keV). Therefore, the virtual monochromatic X-ray images 701 and 751 are images having mutually different energy levels. By performing material discrimination processing using the virtual monochromatic X-ray images 701 and 751, the water density image 301 and iodine density image 401 can be generated.

Next, another virtual monochromatic X-ray image 702 is selected from the input image set 700, and then a virtual monochromatic X-ray image 752 is selected from the output image set 750, which is inferred based on the virtual monochromatic X-ray image 702. Furthermore, the water density image 302 and iodine density image 402 are generated based on the virtual monochromatic X-ray image 702 and the virtual monochromatic X-ray image 752.

In the same manner below, a water density image and an iodine density image are generated based on the virtual monochromatic X-ray image selected from the input image set 700 and the virtual monochromatic X-ray image selected from the output image set 750. In this manner, the image set 300 containing the water density images 301 to 30$z$ and the image set 400 containing the iodine density images 401 to 40$z$ can be generated. Therefore, the water density images in the image set 300 and iodine density images in the image set 400 can be generated based on the virtual monochromatic X-ray images in the input image set 700 and the virtual monochromatic X-ray images in the output image set 750 inferred by the first trained neural network 84.

The image sets 300 and 400 are prepared as training data to be used as input for the second neural network 93, as depicted in FIG. 8. Next, the image sets 500 and 600 (see FIG. 8) used as training data for the second neural network 93 are described.

FIG. 10 is an explanatory diagram of the image sets 500 and 600. The image set 500 contains the water density images 501 to 50$z$, and the image set 600 contains the iodine density images 601 to 60$z$. The water density images 501 to 50$z$ and iodine density images 601 to 60$z$ form pairs P1 to Pz. Each pair represents a pair including a water density image and iodine density image discriminated, for example, by performing material discrimination processing with respect to dual energy CT data. For example, the pair P1 represents a pair including the water density image 501 and iodine density image 601 discriminated, for example, by performing material discrimination processing with respect to dual energy CT data. Furthermore, the pair P2 represents a pair including the water density image 502 and iodine density image 602 discriminated, for example, by performing material discrimination processing with respect to dual energy CT data. In the same manner below, each of the other pairs P3 to Pz represents a pair including a water density image and iodine density image discriminated, for example, by performing material discrimination processing with respect to dual energy CT data.

The water density images 501 to 50$z$ and iodine density images 601 to 60$z$ can be obtained, for example, from a medical institution that actually scans a patient with a CT system compatible with dual energy CT.

Thereby, the second training data set 90 (image sets 300 to 600) can be prepared, as depicted in FIG. 8. After preparing the second training data set 90, the flow proceeds to step ST92 (see FIG. 4). In step ST92, the second trained neural network 94 is created using the second training data set 90.

Figure 11:
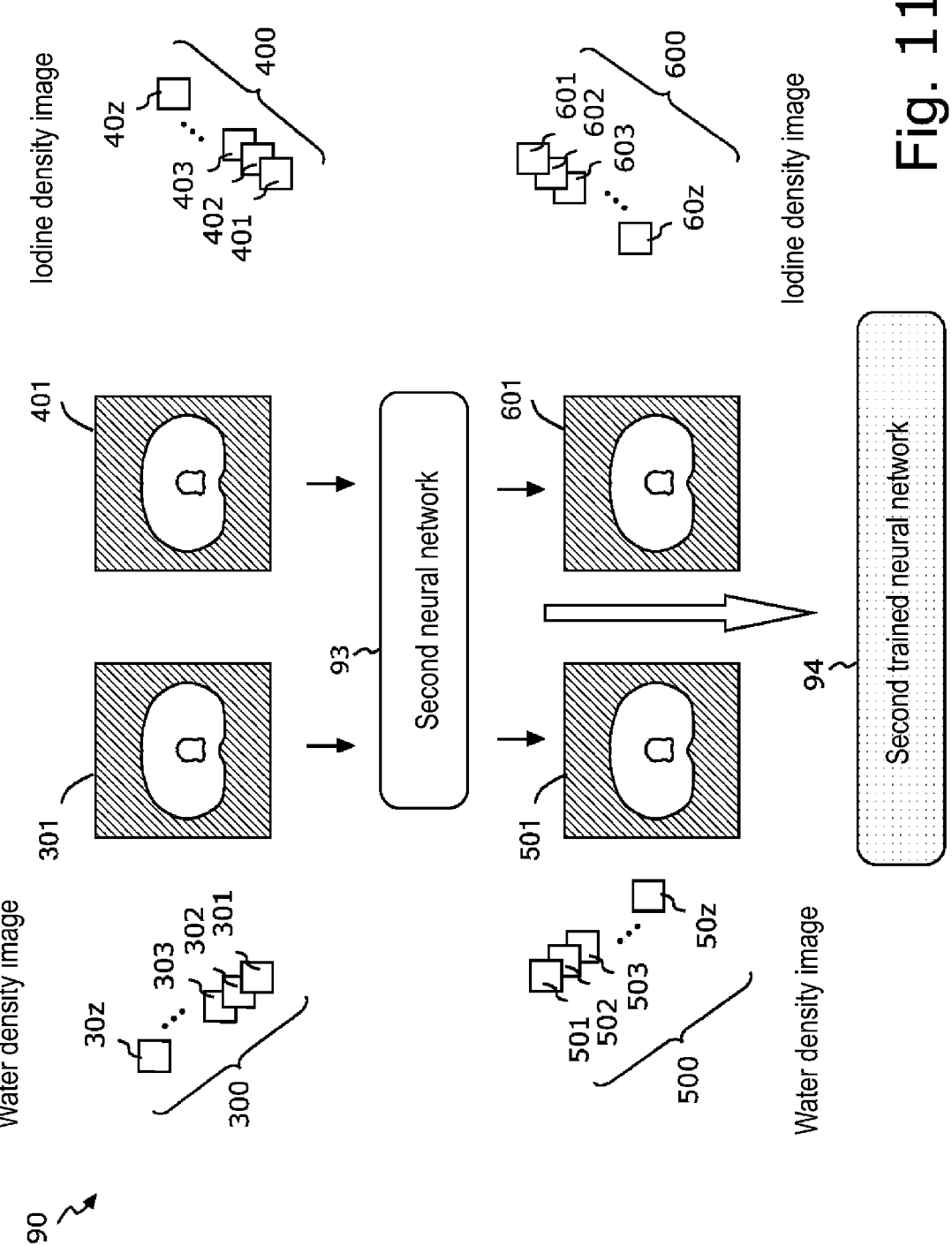
FIG. 11 is an explanatory diagram of a method of creating a second trained neural network 94.

FIG. 11 is an explanatory diagram of the method of creating the second trained neural network 94. The second trained neural network 94 is generated by the second neural network 93 performing learning using the second training data set 90.

First, the water density image 301 is selected from the image set 300. Furthermore, the iodine density image 401, which was generated together with the water density image 301 in step ST912 (see FIG. 9), is selected from the image set 400. Furthermore, the water density image 501 is selected from the image set 500. Furthermore, the iodine density image 601 is selected from the image set 600, which forms a pair with the water density image 501. Furthermore, the second neural network 93 performs learning using the water density image 301 and iodine density image 401 pair and the water density image 501 and iodine density image 601 pair, such that the water density image 301 and iodine density image 401 pair is used as input for the second neural network 93, and the water density image 501 and iodine density image 601 pair is output from the second neural network 93.

In the same manner below, learning is performed such that a pair of a water density images selected from the image set 300 and an iodine density image selected from the image set 400 is input to the second neural network 93 and a pair of a water density image selected from the image set 500 and an iodine density image selected from the image set 600 is output from the second neural network 93. Thereby, training can be performed using the second training data set 90, which includes the image sets 300 to 600, to create the second trained neural network 94. Note that in the present embodiment, the neural network 93 learns a pair of a water density image and iodine density image, but the water density and iodine density images may be separately learned. Furthermore, there is an inverse correlation between water and iodine; therefore, training of the neural network 93 may be performed in consideration of this relationship.

In the present embodiment, the first and second trained neural networks 84 and 94, created as described above, are used to infer a water density image and iodine density image. A flow of inferring a water density image and iodine density image using the trained neural networks 84 and 94 is described below, with reference to the flow in FIG. 4.

Figure 12:
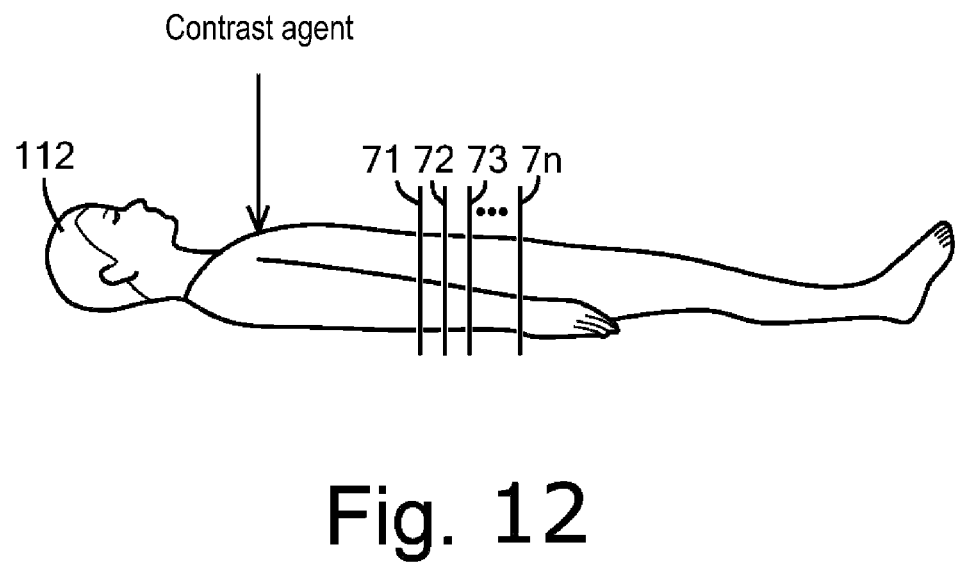

At step ST1, a subject body scan is performed. Specifically, as depicted in FIG. 12, a contrast agent is injected into the subject body 112 and a contrast-enhanced CT scan is performed using the CT system 100 to acquire a contrast-enhanced image of the imaging site of the subject body 112. Herein, a scan is performed to acquire contrast-enhanced images of slices 71 to 7*n* set with respect to the imaging site of the subject body 112. Note that the tube voltage during scanning is 120 kVp.

The data obtained from the scan is collected by the DAS 214 (see FIG. 2), and the collected data is transmitted to the computer 216 or image reconstruction unit 230. Step ST2 (see FIG. 4) is then performed. In step ST2, the processor of the computer 216 or image reconstructor 230 generates CT images 11 to in (CT image set 10) of the slices 71 to 7*n* (see FIG. 12) of the imaging site based on the data collected from the subject body in step ST1. In FIG. 4, only the CT image 11 is enlarged of the CT images 11 to 1*n*. After generating the CT images 11 to 1*n*, the flow proceeds to step ST3.

In step ST3, the processor of the computer 216 inputs the CT image to the first trained neural network 84 and causes the first trained neural network 84 to infer a virtual monochromatic X-ray image of 50 (keV). In FIG. 4, the CT image 11 is input to the first trained neural network 84, and the first trained neural network 84 is depicted inferring the virtual monochromatic X-ray image 21 of 50 (keV).

In step ST4, the processor of the computer 216 generates the first material density image 31 and the second material density image 41 based on the CT image 11 and the inferred virtual monochromatic X-ray image 21 of 50 (keV). Herein, the first material density image 31 is a water density image, and the second material density image 41 is an iodine density image.

In step ST5, the processor of the computer 216 inputs the water density image 31 and iodine density image 41 pair calculated in step ST4 to the second trained neural network 94 to infer the water density image 51 and iodine density image 61 pair. Therefore, the water density image 51 and iodine density image 61 can be inferred from the CT image 11.

In the same manner below, the processor of the computer 216 also inputs each of the other CT images 12 to in to the first trained neural network 84 as input images, and infers a water density image and an iodine density image for each CT image. Therefore, water density images and iodine density images can be inferred for the CT images 11 to 1*n*. Note that for convenience of explanation, only the water density image 51 and iodine density image 61 inferred for the CT image 11 are depicted in FIG. 4, and water density images and iodine density images inferred for the other CT images 12 to in are omitted. The operator displays the inferred water density image and iodine density image on the display part and checks each image. Thus, the flow shown in FIG. 4 is completed.

In the present embodiment, the first trained neural network 84 and second trained neural network 94 are created in a training phase. The first trained neural network 84 is created by the first neural network 83 performing learning using a plurality of virtual monochromatic X-ray images. Thus, the first trained neural network 84 is configured to perform inference processing in a CT value domain. Furthermore, the CT image 11 is input to the first trained neural network 84 to infer the virtual monochromatic X-ray image 21. The CT image 11 corresponds to a virtual monochromatic X-ray image of 70 (keV), and the virtual monochromatic X-ray image 21 inferred by the first trained neural network 84 is a virtual monochromatic X-ray image of 50 (keV). Therefore, the CT image 11 and virtual monochromatic X-ray image 21 are images having mutually different energy levels. The first and second material density images, namely, the water density image 31 and iodine density image 41 can be generated by performing material discrimination processing using the CT image 11 and virtual monochromatic X-ray image 21.

However, the virtual monochromatic X-ray image 21 used to calculate the water density image 31 and iodine density image 41 are inferred from the CT image 11 generated based on single energy CT data. In general, a virtual monochromatic X-ray image inferred based on single energy CT data is somewhat less accurate in terms of CT values than a virtual monochromatic X-ray image calculated based on dual energy CT data. Therefore, if the water density image 31 and iodine density image 41 are calculated based on the CT image 11 and the virtual monochromatic X-ray image 21, the accuracy of the water density image 31 and iodine density image 41 is also limited.

Thus, in the present embodiment, in addition to the first trained neural network 84, a second trained neural network 94 is created, which performs inference processing in the density domain. The second trained neural network 94 performs inference processing in the density domain. Therefore, when the water density image 31 and iodine density image 41 generated based on single energy CT data are input to the second trained neural network 94, inference processing is performed in the density domain, and water density image 51 and iodine density image 61 are output. Thus, the second trained neural network 94 can infer the water density image 51 and iodine density image 61 that are more reliable than the water density image 31 and the iodine density image 41 in terms of calculated density of reference materials.

Note that in the present embodiment, in step ST5, one second trained neural network 94 is used to infer a water density image and iodine density image. However, a water density image and iodine density image may be inferred using separate trained neural networks (see FIG. 13).

Figure 13:
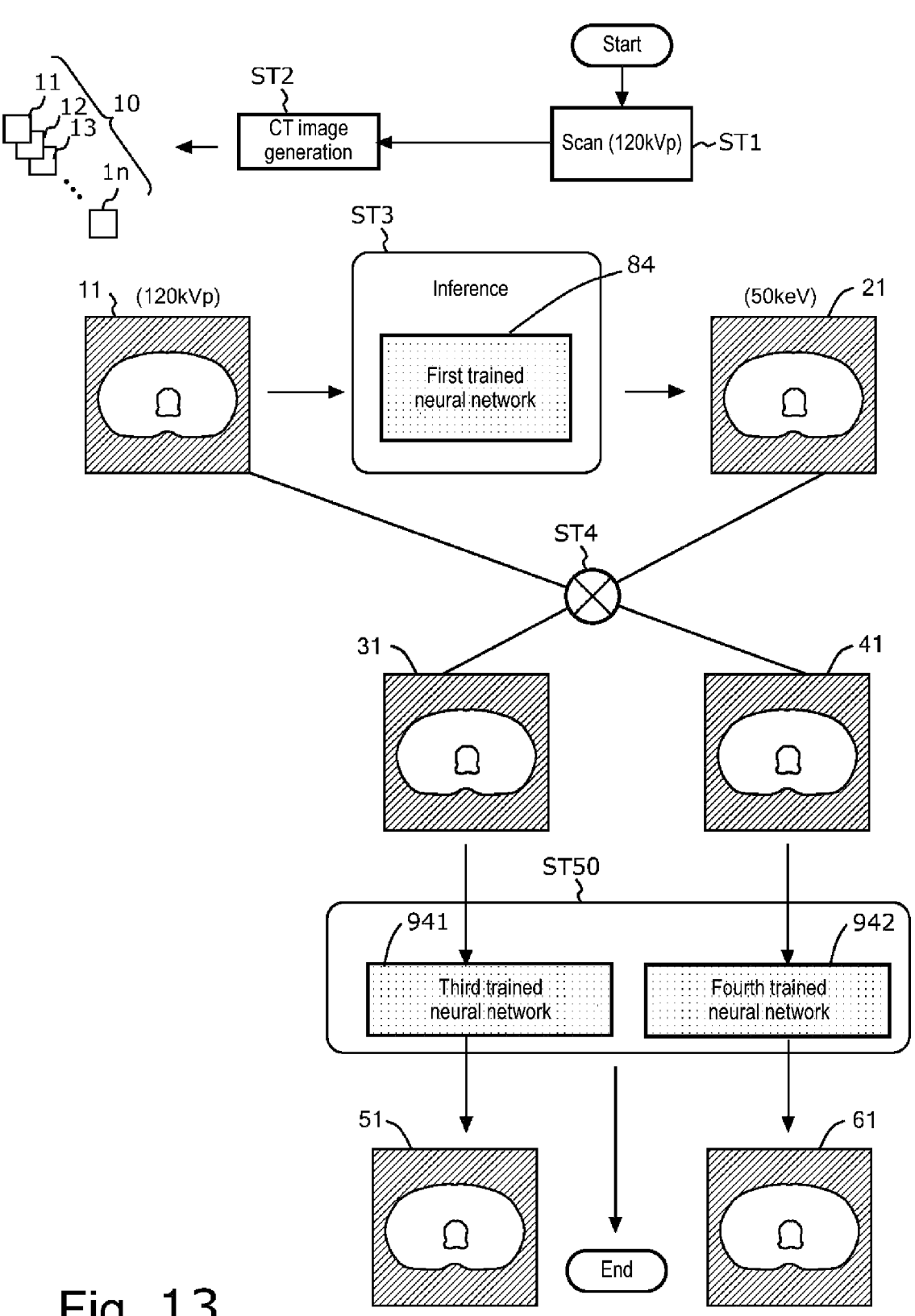
FIG. 13 is a flowchart of an example of inferring a water density image and iodine density image using separate trained neural networks.

FIG. 13 is a flowchart of an example of inferring a water density image and iodine density image using separate trained neural networks. In FIG. 13, steps ST1 to ST4 are the same as steps ST1 to ST4 depicted in FIG. 4; therefore, the description of steps ST1 to ST4 is omitted with step ST50 being mainly described.

In step ST50, inference of a water density image and iodine density image is performed using a third trained neural network 941 and a fourth trained neural network 942.

The third trained neural network 941 is created by a third neural network (not depicted) performing learning using the water density images 301 to 30*z* (image set 300) and water density images 501 to 50*z* (image set 500) depicted in FIG. 8. Furthermore, the fourth trained neural network 942 is created by a fourth neural network (not depicted) performing learning using the iodine density images 401 to 40*z* (image set 400) and iodine density images 601 to 60*z* (image set 600) depicted in FIG. 8.

In step ST50, the processor of the computer 216 inputs the water density image 31 calculated in step ST4 to the third trained neural network 941 to infer the water density image 51. Furthermore, the processor of the computer 216 inputs the iodine density image 41 calculated in step ST4 to the fourth trained neural network 942 to infer the iodine density image 61.

Therefore, the water density image 51 and iodine density image 61 can be inferred from the CT image 11.

In the same manner below, the processor of the computer 216 inputs each of the other CT images 12 to in to the first trained neural network 84 as input images, and infers a water density image and an iodine density image for each CT image. Therefore, water density images and iodine density images can be inferred for the CT images 11 to in. Thus, a water density image and iodine density image may be inferred using the two separate trained neural networks 941 and 942.

Note that in the present embodiment, the virtual monochromatic X-ray image of 70 (keV) is used as input for the neural network 83 during the training phase (see FIG. 7). However, a virtual monochromatic X-ray image having an energy level different from 70 (keV) may be used as the input of the neural network 83. For example, if the CT system 100 uses other tube voltages instead of 120 kVp, a virtual monochromatic x-ray image having a different energy level than 70 (keV) can be used as the input of the neural network 83 to perform training of the neural network 83. For example, if the tube voltage of the CT system 100 is 140 kVp instead of 120 kVp, a virtual monochromatic X-ray image of 75 (keV) can be used as the input of the neural network 83, since 140 kVp corresponds to an energy level of approximately 75 (keV). Therefore, if the tube voltage of the CT system 100 is 140 kVp, virtual monochromatic X-ray images having energy levels of 75 (keV) and 50 (keV), for example, can be prepared as training data. Furthermore, training of the neural network 83 can be performed, such that the virtual monochromatic X-ray image of 75 (keV) is used as input for the neural network 83 and the virtual monochromatic X-ray image of 50 (keV) is output from the neural network 83.

In the present embodiment, the first trained neural network 84 is created based on training data obtained from a contrast-enhanced CT scan. However, the present invention is not limited to the example of creating the trained neural network 84 based on training data obtained from a contrast-enhanced CT scan, and the trained neural network 84 for inferring a virtual monochromatic X-ray image based on training data obtained by a non-contrast-enhanced scan may be created.

What is claimed is:

1. A device, comprising one or more processors for performing an operation, the operation including:

inputting a CT image generated based on single energy CT data collected from a subject body into a first trained neural network, the first trained neural network being created by a first neural network performing learning using a plurality of virtual monochromatic X-ray images in a training phase;

causing the first trained neural network to infer a virtual monochromatic X-ray image based on the CT image;

generating a first material density image expressing the density of a first reference material and a second material density image expressing the density of a second reference material based on the CT image and the virtual monochromatic X-ray image inferred by the first trained neural network;

inputting the first material density image and second material density image into a second trained neural network, the second trained neural network being created by a second neural network performing learning using a plurality of material density images in a training phase; and causing the second trained neural network to infer a third material density image expressing the density of the first reference material and a fourth material density image expressing the density of the second reference material based on the first material density image and second material density image.

2. The device according to claim 1, wherein the first trained neural network is created by a first neural network performing learning using a first training data set in a training phase, the first training data set contains a first image set containing a first plurality of virtual monochromatic X-ray images and a second image set containing a second plurality of virtual monochromatic X-ray images, and each virtual monochromatic X-ray image of the first plurality of virtual monochromatic X-ray images is a virtual monochromatic X-ray image of a first energy level corresponding to the tube voltage of a CT system that collects single energy CT data, and each virtual monochromatic X-ray image of the second plurality of virtual monochromatic X-ray images is a virtual monochromatic X-ray image of a second energy level.

3. The device according to claim 2, wherein the first trained neural network is created by the first neural network performing learning using the first training data set, such that in a training phase, each virtual monochromatic X-ray image of the first plurality of virtual monochromatic X-ray images is used as input for the first neural network, and each virtual monochromatic X-ray image of the second plurality of virtual monochromatic X-ray images is output from the first neural network.

4. The device according to claim 1, wherein the second trained neural network is created by a second neural network performing learning using a second training data set containing a plurality of material density images set in a training phase, and the second training data set contains: a third image set containing a first plurality of material density images expressing the density of a first reference material; a fourth image set containing a second plurality of material density images expressing the density of a second reference material; a fifth image set containing a third plurality of material density images expressing the density of the first reference material; and a sixth image set containing a fourth plurality of material density images expressing the density of the second reference material.

5. The device according to claim 4, wherein each virtual monochromatic X-ray image of the first plurality of material density images and each virtual monochromatic X-ray image of the second plurality of material density images are images generated based on a virtual monochromatic X-ray image inferred by the first trained neural network.

6. The device according to claim 5, wherein the third image set containing the first plurality of material density images and the fourth image set containing the second plurality of material density images are generated based on:

an input image set containing a plurality of virtual monochromatic X-ray images input into the first trained neural network, each virtual monochromatic X-ray image of the input image set being a virtual monochromatic X-ray image of the same energy level as the first plurality of virtual monochromatic X-ray images used when creating the first trained neural network; and an output image set containing a plurality of virtual monochromatic X-ray images inferred by the first trained neural network, each virtual monochromatic X-ray image of the output image set being a virtual monochromatic X-ray image inferred from each virtual monochromatic X-ray image of the input image set being input into the first trained neural network.

7. The device according to claim 6, wherein each material density image of the third plurality of material density images and each material density image of the fourth plurality of material density images are images generated based on dual energy CT data.

8. The device according to claim 7, wherein the second trained neural network is created by the second neural network performing learning using the first plurality of material density images, second plurality of material density images, third plurality of material density images, and fourth plurality of material density images, such that in a training phase, each material density image of the first plurality of material density images and each material density image of the second plurality of material density images are used as input for the second neural network and each material density image of the third plurality of material density images and each material density image of the fourth plurality of material density images is output from the second neural network.

9. The device according to claim 1, wherein the first reference material is water, and the second reference material is iodine.

10. A CT system for collecting single energy CT data, comprising:
   an X-ray tube in which a prescribed tube voltage is applied; and
   one or more processors, wherein
   the one or more processors performs an operation, the operation including:
   generating a CT image based on single energy CT data collected from a subject body;
   inputting the CT image into a first trained neural network,
      the first trained neural network being created by a first neural network performing learning using a plurality of virtual monochromatic X-ray images in a training phase;
      causing the first trained neural network to infer a virtual monochromatic X-ray image based on the CT image;
   generating a first material density image expressing the density of a first reference material and a second material density image expressing the density of a second reference material based on the CT image and the virtual monochromatic X-ray image inferred by the first trained neural network;
      inputting the first material density image and second material density image into a second trained neural network,
      the second trained neural network being created by a second neural network performing learning using a plurality of material density images in a training phase; and
   causing the second trained neural network to infer a third material density image expressing the density of the first reference material and a fourth material density image expressing the density of the second reference material based on the first material density image and second material density image.

11. The CT system according to claim 10, wherein the first trained neural network is created by the first neural network learning a first training data set in a training phase,
   the first training data set containing a first image set containing a first plurality of virtual monochromatic X-ray images and a second image set containing a second plurality of virtual monochromatic X-ray images, and
   each virtual monochromatic X-ray image of the first plurality of virtual monochromatic X-ray images is a virtual monochromatic X-ray image of a first energy level corresponding to the predetermined tube voltage, and each virtual monochromatic X-ray image of the second plurality of virtual monochromatic X-ray images is a virtual monochromatic X-ray image of a second energy level.

12. The CT system according to claim 11, wherein the second trained neural network is created by a second neural network performing learning using a second training data set containing a plurality of material density images set in a training phase, and
   the second training data set contains: a third image set containing a first plurality of material density images expressing the density of a first reference material; a fourth image set containing a second plurality of material density images expressing the density of a second reference material; a fifth image set containing a third plurality of material density images expressing the density of the first reference material; and a sixth image set containing a fourth plurality of material density images expressing the density of the second reference material.

13. A method of creating a trained neural network, comprising the steps of:
   creating a first trained neural network,
   the first trained neural network being created by a first neural network performing learning using a first training data set,
      the first training data set containing a first image set containing a first plurality of virtual monochromatic X-ray images and a second image set containing a second plurality of virtual monochromatic X-ray images,
      each virtual monochromatic X-ray image of the first plurality of virtual monochromatic X-ray images being a virtual monochromatic X-ray image of a first energy level corresponding to a tube voltage of a CT system that collects single energy CT data, and each virtual monochromatic X-ray image of the second plurality of virtual monochromatic X-ray images being a virtual monochromatic X-ray image of a second energy level, and
      the first neural network performing learning using the first training data set, such that each virtual monochromatic X-ray image of the first plurality of virtual monochromatic X-ray images is used as input for the first neural network and each virtual monochromatic X-ray image of the second plurality of virtual monochromatic X-ray images is output from the first neural network; and
   creating a second trained neural network,
   the second trained neural network being created by a second neural network performing learning using a second training data set,
      the second training data set containing a third image set containing a first plurality of material density images expressing the density of a first reference material, a fourth image set containing a second plurality of material density images expressing the density of a second reference material, a fifth image set containing a third plurality of material density images expressing the density of the first reference material, and a sixth image set containing a fourth plurality of material density images expressing the density of the second reference material,
      each virtual monochromatic X-ray image of the first plurality of material density images and each virtual monochromatic X-ray image of the second plurality of material density images being images generated based on a virtual monochromatic X-ray image inferred by the first trained neural network, each material density image of the third plurality of material density images and each material density image of the fourth plurality of material density images being images generated by dual energy CT data, and the second neural network performing learning using the first plurality of material density images, second plurality of material density images, third plurality of material density images, and fourth plurality of material density images, such that each material density image of the first plurality of material density images and each material density image of the second plurality of material density images is used as input for the second neural network and each material density image of the third plurality of material density images and each material density image of the fourth plurality of material density images is used as output from the second neural network.

\* \* \* \* \*